US000001986H

(19) United States

(12) Statutory Invention Registration (10) Reg. No.: US H1986 H

Atlas et al. (43) Published: Aug. 7, 2001

(54) METHOD FOR REMOVING ORGANIC SULFUR FROM HETEROCYCLIC SULFUR-CONTAINING ORGANIC COMPOUNDS

(76) Inventors: Ronald M. Atlas, 1603 Dunbarton Wynde, Louisville, KY (US) 40205; David J. Boron, 3765 Hetten La., Woodbridge, VA (US) 22193; William R. Deever, 895 Brandywine Dr., Beaumont, TX (US) 77706; Axel R. Johnson, 567 Benjamin Rd., N. Babylon, NY (US) 11703; Beverly Lynn McFarland, 1143 Halifax Ave., Davis, CA (US) 95616; Jarold A. Meyer, 849 Corte Briones, Martinez, CA (US) 94553

(21) Appl. No.: 09/307,531

(22) Filed: May 7, 1999

(51) Int. Cl.[7] ..... B09B 3/00; C12N 11/04; C12N 1/00

(52) U.S. Cl. ..... 435/262.5; 435/182; 435/822

(58) Field of Search ..... 435/262.5, 182, 435/822

(56) References Cited

U.S. PATENT DOCUMENTS 5,874,294 * 2/1999 Valentine ..... 435/282

* cited by examiner

*Primary Examiner*—Charles T. Jordan
*Assistant Examiner*—Aileen J. Baker
(74) *Attorney, Agent, or Firm*—Alston & Bird LLP

(57) ABSTRACT

A method for removing sulfur from liquid compositions containing aliphatic or cylic organic sulfur-containing compounds, e.g., dibenzothiophene includes activating the sulfur-containing compound by oxidizing either the organic sulfur or adjacent carbon atoms in the presence of a suitable active biocatalyst (ie., microorganism, enzyme, etc.) followed by treating of the activated compound by techniques such as fluidized catalytic cracking so as to remove the sulfur therefrom.

16 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR REMOVING ORGANIC SULFUR FROM HETEROCYCLIC SULFUR-CONTAINING ORGANIC COMPOUNDS

BACKGROUND OF THE INVENTION

The present invention relates to a method for removing organic sulfur from a liquid composition containing sulfur-containing organic compounds. This method can be employed in the production of transportation fuels and, in particular, gasoline and diesel fuels produced by the fluidized catalytic cracking of a feedstock.

The auto industry has long been faced with the problems associated with sulfur in fuels and, in particular, transportation fuels. These problems have largely crystallized around three areas, first, the degradation or poisoning of catalyst employed in emission control systems. Second, the problems associated with sulfur monitoring, i.e., false sensor readings relating to catalyst performance. To this end, recent amendments to the Clean Air Act will require the automotive industry to equip future vehicles with onboard diagnostic devices that can measure the effectiveness of catalyst emission controls for 100,000 miles. The diagnostic devices will measure oxygen storage capacity to determine catalyst efficiency. The sulfur in gasoline can interfere with this oxygen storage measurement causing the sensor to show an erroneous decrease in catalyst efficiency. In order to prevent these erroneous readings, the sulfur content of gasoline should be no more than 50 ppm.

Third, sulfur dioxide emissions are a precursor to the formation of sulfate aerosols which are believed to play a substantial role in the total amount of ambient "fine particulate" matter. Moreover, recent epidemiological studies cited through the EPA suggest that sulfate aerosols are at least a contributory constituent of 2.5-micron particulate matter. Thus, the need to reduce sulfur emissions is also tied -at least in part-to ongoing efforts to reduce the emission of 2.5-micron particulate matter.

In modern refineries, fuels are produced from a number of streams. A primary source of sulfur-containing organic compounds in the gasoline pool is FCCU gasoline, i.e., gasoline produced in a fluidized catalytic cracking unit. The primary source of sulfur in FCCU fuels is thiophenic sulfur comprised of dibenzothiophene, benzothiophene, and thiophene and their various derivatives.

In order to produce a low sulfur FCCU fuel, the art has focused on either (i) hydrotreating the FCCU feed or (ii) treating the FCCU product for sulfur removal. Neither of these techniques, however, have been entirely effective.

The hydroprocessing of FCCU feed has been in commercial practice for over thirty years. In this regard, FCCU fuels have a high octane number due -at least in part-to the olefin content of the lighter, lower-boiling fraction. The hydrotreatment of FCCU fuels for sulfur removal can, however, result in a significant loss of efficiency. For example in gasolines, $R+M_2$ octane losses of 3–10 numbers or more can result depending on the severity of the hydrotreatment.

Moreover, hydrotreatment to a sulfur level of, e.g., 50 ppm, can be cost prohibitive. In particular, the costs of decreasing sulfur content from 500 ppm to 200 ppm by desulfurizing heavy FCCU fuels can be on the order of about one cent per gallon. However, the next increment of decrease in sulfur, e.g., from 200 ppm to 50 ppm, can be on the order of four cents a gallon. This cost is only further increased in those instances where processing, e.g., isomerization, is needed to offset fuel efficiency loss during hydrotreatments.

Separately, microorganisms have been employed in processes for removing organic sulfur from certain thiophenic compounds.

The biological pathways employed are either "carbon-destructive" which results in the overall degradation of the compound or "sulfur-specific" which results in the selective attack on the sulfur atom. A preferred sulfur specific process involves four enzymatic steps of "sulfoxide-sulfane-sulfonate-sulfate" and is hence termed the "4S pathway". The 4S pathway is illustrated in FIG. 1*a*–1*d*. Attention in this regard is directed towards the article entitled "Desulfurization of Coal: The Microbial Solution", Trends Biotechnol., 7,97-101, April 1989, by J.J. Kilbane, that discusses the 4S pathway in detail. Attention is also directed towards U.S. Pat. Nos. 5,496,720; 5,510,265; and 5,529,930, which are all incorporated by reference in their entirety for all purposes.

For example, non-commercial techniques for the desulfurization of diesel fuel have employed biocatalysts such as *Rhodococcus erythropilis,* which catalysts produce enzymes capable of selectively oxidizing sulfur found in heterocyclic sulfur-containing organic compounds, such as dibenzothiophene (DBT), to sulfone. The sulfur is then "clipped" from the molecules to produce an oxygenated, sulfur-free derivative of biphenyl and inorganic sulfate.

Although biocatalytic oxidation by way of the 4S pathway is capable of removing sulfur in diesel fuels, it has been severely limited both in terms of its applicability and its effectiveness. In particular, biodesulfurization as it exists in the art is currently focused on the desulfurization of diesel fuels not gasolines. Moreover, biodesulfurization has suffered from the same cost and octane problems that can be associated with traditional hydroprocessing. In light of these problems, it has not found commercial success.

Accordingly, the need still exists for a method of removing sulfur-containing compounds from feed streams for fuels and, in particular, FCCU fuels.

SUMMARY OF THE INVENTION

The present invention is based at least in part on the surprising discovery that biocatalytic oxidation by way of the 4S pathway which is halted prior to the last of the four enzymatic steps, is capable of providing an activated sulfur-containing compound that can be subsequently treated to remove the sulfur. Moreover, this process can effectively remove sulfur at a reduced cost and without the disadvantages, e.g., fuel performance loss, associated with traditional catalytic or biodesulfurization techniques.

To this end, one aspect of the invention relates to a process for removing sulfur which includes oxidizing a heterocyclic sulfur-containing compound so as to introduce an oxygen atom to the sulfur heteroatom ring structure. The process further includes the subsequent removal of the sulfur therefrom.

In one embodiment, the method according to the invention comprises:

(a) providing a liquid composition containing an aliphatic and/or heterocyclic sulfur-containing organic compound;

(b) activating the heterocyclic sulfur-containing organic compound by oxidizing either the organic sulfur or carbon atom adjacent to the sulfur;

(c) treating the activated compound so as to remove sulfur therefrom.

The method according to the present invention preferably employs an active biocatalyst in connection with step (b) but not in connection with step (c).

The biocatalyst can be whole cell living microorganisms, lyophilized cells, cell parts or enzymes. The biocatalyst can be immobilized and operate in aqueous or non-aqueous mediums. The source of the biocatalyst can be any bacteria or microorganism with the capability to oxidize sulfur to the sulfoxide, sulfone, or sulfonic acid.

In a preferred embodiment, the activation step (b) involves the use of a biocatalyst suitable for providing the enzymatic 4S pathway. However, the biocatalytic oxidation is halted prior to the enzymatic 4S step in that pathway. Moreover, step (c) preferably involves fluidized catalytic cracking.

DETAILED DESCRIPTION OF THE PREFERRED EMBODIMENT

As discussed above, the invention relates to a method for removing organic sulfur from sulfur-containing organic compounds in which oxygen can be added to the sulfur heteroatom structure, irrespective of the substitution or position of the heteroatom in the molecule. The compound can then be effectively treated so as to remove the sulfur therefrom.

In one embodiment, the invention relates to a method for removing organic sulfur from heterocyclic sulfur-containing organic compounds present in liquid composition. This method preferably includes two steps:

(1) activating the heterocyclic sulfur-containing organic compound by oxidizing either the organic sulfur or adjacent carbon atoms, and then;

(2) treating the activated compound so as to remove the sulfur therefrom.

By "activation" it is meant that oxygen is introduced into the molecule at, e.g., the sulfur or carbon adjacent thereto so as to provide reactive sites that will allow subsequent removal of the sulfur. For example, in the making of FCCU gasoline, the activation will provide suitable sites capable of reacting with acidic sites on an FCCU catalyst.

Moreover, oxidation of the organic sulfur will preferably destabilize the associated ring structures and therefore cause the oxygenated intermediates, e.g., oxygenated dibenzothiophenes, to react differently than other compounds in the liquid composition. For example, where a liquid feed containing DBT is used in making FCCU gasoline, the result of the oxygenated site of the DBT coming into contact with the active sites on the FCCU catalyst will be a chemical reaction that would open the ring and preclude the formation of thiophenes or other sulfur compounds in the FCCU catalyst product.

By "treating" is meant that activated compound is reacted under conditions effective to provide for the removal of sulfur from the activated compound. Although this specification will focus on one preferred embodiment which utilizes fluidized catalytic cracking to remove the sulfur, the present invention is by no means limited solely to that particular process step, and could just as effectively employ other elevated temperature, pressure or temperature and pressure reaction system either with or without the use of chemical catalysts.

In the petroleum extraction and refining arts, the term "organic sulfur" is generally understood as referring to organic molecules having a hydrocarbon framework to which one or more sulfur atoms (called heteroatoms) are covalently joined. These sulfur atoms can be joined directly to the hydrocarbon framework, e.g., by one or more carbon-sulfur bonds, or can be present in a substituent joined to the hydrocarbon framework of the molecule, e.g., a sulfonyl group (which contains a carbon-oxygen-sulfur covalent linkage). The general class of organic molecules having one or more sulfur heteroatoms are sometimes referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked to adjacent carbon atoms in the hydrocarbon framework by aromatic carbon-sulfur bonds are referred to as "sulfur-bearing heterocycles". The sulfur that is present in many types of sulfur-bearing heterocycles is often referred to as "thiophenic sulfur" in view of the five-membered aromatic ring in which the sulfur heteroatom is present. The simplest such sulfur-bearing heterocycle is thiophene, which has the composition $C_4H_4S$.

In the context of this invention, the method is suitable for use with any liquid composition containing an organic sulfur-containing compound. Where the desired product is a transportation fuel such as gasoline, the feed can be any petroleum feedstock suitable for making the desired fuel. The choice of feed is also dependent upon the desired end product and the sulfur removal step being employed. For example, where the sulfur removal step includes the fluidized catalytic cracking of the activated compound, the feed is preferably a FCCU feed which can include mid-distillate, gasoline or vacuum gas oil (VGO) derivative.

As discussed above, the first step is the activation step. The activation step preferably comprises the oxidation of the organic sulfur compounds in the presence of an active biocatalyst. The biocatalyst can be whole cell living microorganisms, lyophilized cells, cell parts or enzymes. The biocatalyst can be immobilized and operate in aqueous or non-aqueous mediums. The source of the biocatalyst can be any bacteria or microorganism with the capability to oxidize sulfur to the sulfoxide, sulfone, or sulfonic acid.

The biocatalytic oxidation according to the invention preferably involves halting the 4S pathway prior to the last of the four enzymatic steps. Accordingly, it preferably involves either the 1S, 2S or 3S pathway. The resulting intermediate product is, of course, dependent upon the exact pathway employed. For example, an oxidation process employing the 1S enzymatic step, FIG. 1*a*, will involve the oxidation of, e.g., dibenzothiophene sulfur to the corresponding sulfoxide. Similarly, a process employing the 2S enzymatic step, FIG. 1*b*, will involve the oxidation of the dibenzothiophene sulfur to the corresponding sulfone. Finally, a process including the 3S enzymatic step, FIG. 1*c*, will involve the oxidation of the dibenzothiophene sulfur to the corresponding sulfonic acid.

The preferred biocatalysts are those capable of providing the enzymatic 1S, 2S, 3S or 4S pathways. Suitable biocatalysts for use in this invention include those biocatalysts recognized in the art such as the strain of Rhodococcus bacteria, ATCC 53968 disclosed by Kilbane in U.S. Pat. No. 5,104,801 (which is incorporated herein by reference) and *Rhodococcus erythropilis* as well as mutant strains thereof In fact, the biocatalytic oxidation step of the inventive process allows for a greater selection of microorganisms since there are a larger number of microorganisms capable of performing the 1S, 2S or 3S pathways as compared to the more traditional 4S pathway.

The preferred process conditions associated with the 1S, 2S, and 3S pathways are recognized within the art and as such need not be described in detail here. For example, the article entitled "Desulfurization of Coal: The Microbial Solution", Trends Biotechnol., 7,97-101, April 1989, by J.J.

Kilbane, discusses the 4S pathway in detail. Attention is also once again directed towards U.S. Pat. Nos. 5,496,720; 5,510,265; and 5,529,930. Preferred reaction conditions may employ aqueous or non-aqueous media at ambient or elevated temperatures and/or pressures.

The second step of the sulfur removing process according to this invention, involves the reaction of the activated compounds so as to remove the organic sulfur therefrom. This step preferably does not involve biocatalytic sulfur removal. While it is preferred that a biocatalyst is not present, an inactive biocatalyst can be present during the step.

By "inactive biocatalyst" it is meant that, sulfur removal occurs under reactive conditions where any biocatalyst that is present is not in active form. For example, the activated feed stream could be subjected to sulfur removal prior to removal of the biocatalyst therefrom. Such a process would provide cost savings insofar as it would not be necessary to remove the biocatalyst therefrom. Other than that restriction, there are no other restrictions on this step. However, as discussed above, this step preferably comprises the fluidized catalytic cracking of the activated feedstream.

As fluidized catalytic cracking is well recognized in the art, it need not be described in detail here. However, it is important to recognize that any suitable fluidized catalytic cracking process and/or FCC catalyst can be effectively employed in the context of this invention.

The fluidized catalytic cracking process would effectively remove the sulfur from the activated compound which sulfur would exit the reactor in the form of an overhead stream, e.g., $H_2S$, or on the catalyst as a coke deposit.

In the field of petroleum processing, the inventive method is capable of cost effectively reducing the sulfur content of fossil fuel feedstreams to the order of 50 ppm or even lower.

The inventive method is further capable of providing this significant reduction in sulfur while providing a number of advantages over those traditional processes. First of all, the method can provide a simplified biocatalytic process. To this end, the invention effectively eliminates at least one of the enzymatic steps from traditional 4S pathways. The "simplification" not only results in shorter residence time and hence smaller reactors, but it can also increase system reliability. Accordingly, both capital and operating costs can be decreased.

Because sulfur is not removed during biodesulfurization, additional cost savings can be provided. That is, by eliminating the sulfur in, for example, a fluidized catalytic cracking unit in the form of an $H_2S$ stream or coke on the FCCU catalyst, a decrease in operating cost can be provided.

Finally, the present invention is capable of providing a reduced stacked emissions as compared to prior art removal techniques. This can further decrease the operating cost of the system.

While the present invention has been described in terms of certain preferred embodiments, it should be recognized that various modifications, substitutions, omissions, changes and the like may be made without departing from the spirit of the invention. Accordingly, the scope of the invention is limited only by the scope of the following claims.

What is claimed is:

1. A method for removing organic sulfur from a liquid composition containing aliphatic and/or heterocyclic sulfur-containing organic compounds comprising:

(a) providing a liquid composition containing a sulfur-containing organic compound;

(b) activating said sulfur-containing organic compound by oxidizing at least one of (i) a sulfur atom or (ii) a carbon atom adjacent to the sulfur atom so as to provide an activated compound said oxidizing step is performed in the presence of an active biocatalyst capable of oxidizing sulfur to sulfoxide, sulfone, or sulfonic acid; and (c) removing sulfur from the activated compound.

2. The method according to claim 1 wherein the biocatalyst is a whole-cell microorganism, lyophilized cell or enzyme

3. The method according to claim 1 wherein the biocatalyst is ATCC 53968 or *Rhodococcus erythropilis*.

4. The method according to claim 1 wherein activating step (b) comprises the 1S enzymatic step but not the 4S enzymatic step.

5. The method according to claim 4 wherein activating step (b) further comprises the 2S enzymatic step.

6. The method according to claim 5 wherein activating step (b) further comprises a 3S enzymatic step.

7. The method according to any one of claims 1–6 wherein treating step (c) comprises fluidized catalytic cracking of the liquid composition.

8. The method according to any one of claims 1–6 wherein step (c) comprises the use for elevated temperature and/or pressure reaction systems with or without the use of a chemical catalyst.

9. The method according to claim 1 wherein the liquid composition comprises dibenzothiophene, benzothiophene and aliphatic or heterocyclic derivatives thereof.

10. The method according to claim 1 wherein the liquid composition comprises a fossil fuel.

11. The method according to claim 10 wherein the stream comprises vacuum gas oil.

12. The method according to claim 1 wherein step (b) employs an aqueous medium.

13. The method according to claim 1 wherein the step (b) employs a non-aqueous medium.

14. A method for making FCCU gasoline form a feed stream containing at least one organic sulfur-containing compound comprising:

(a) activating the at least one organic sulfur-containing compound by oxidizing at least one of (i) a sulfur atom or (ii) a carbon atom adjacent to the sulfur atom in the presence of a biocatalyst capable of oxidizing sulfur to sulfoxide, sulfone, or sulfonic acid; and (b) removing sulfur from the activated compound.

15. A product produced by the process according to claim 1.

16. A FCCU fuel produced by the process according to claim 7.

* * * * *